(12) United States Patent
Candau et al.

(10) Patent No.: US 6,616,919 B2
(45) Date of Patent: Sep. 9, 2003

(54) DIBENZOYLMETHANE SUNSCREEN COMPOSITIONS CONTAINING PHOTOSTABILIZING AMOUNTS OF TRI-SUBSTITUTED BUTANE COMPOUNDS

(75) Inventors: Didier Candau, Bievres (FR); Fabien Aubert, Paris (FR)

(73) Assignee: Societe l'Oreal S.A., Paris (FR)

( * ) Notice: Subject to any disclaimer, the term of this patent is extended or adjusted under 35 U.S.C. 154(b) by 0 days.

(21) Appl. No.: 10/228,304

(22) Filed: Aug. 27, 2002

(65) Prior Publication Data

US 2003/0124071 A1 Jul. 3, 2003

(30) Foreign Application Priority Data

Aug. 27, 2001 (FR) .............................. 01 11139

(51) Int. Cl.$^7$ .............................. A61K 7/42; A61K 7/00; A61K 7/44
(52) U.S. Cl. .............................. 424/59; 424/60; 424/400; 424/401
(58) Field of Search .............................. 424/59, 60, 400, 424/401

(56) References Cited

FOREIGN PATENT DOCUMENTS

FR        2 384 842 A       10/1978

OTHER PUBLICATIONS

M.C. Martini et al., "Actifs et Adiitifs en Cosmetologie", XP–002203973, Lavoisier Tec & Doc, Paris, 1992, ppg. 190–195.

G. M. Lazar et al., "Indoor/Outdoor Sunscreens Evaulation by the Stripping Method", XP–001074039, Proceedings of the International Symposium on Controlled Release of Bioactive Materials, Controlled Release Society, Inc., 24, 1997, ppg. 917–918.

French Search Report corresponding to FR 01/11139 completed Jun. 28, 2002, 2 pages.

*Primary Examiner*—Shelley A. Dodson
(74) *Attorney, Agent, or Firm*—Burns, Doane, Swecker & Mathis, L.L.P.

(57) ABSTRACT

Improvedly photostable UV-photoprotecting cosmetic/dermatological compositions for the skin and/or the hair contain (a) a UV-photoprotective amount of at least one dibenzoylmethane sunscreen, e.g., 4-(tert-butyl)-4'-methoxydibenzoylmethane or 4-isopropyldibenzoylmethane, advantageously (a') a UV-photoprotective amount of at least one 1,3,5-triazine sunscreen, e.g., 2-[(p-(tert-butylamido]-4,6-bis[(p-(2'ethylhexyl-1'-oxycarbonyl)anilino]-1,3,5-triazine or 2,4,6-tris[p-(2'-ethylhexyl-1'-oxycarbonyl)anilino]-1,3,5-triazine, (b) an effective sunscreen photostabilizing amount of 1,1,1-tris(2-methyl-4-hydroxy-5-tert-butylphenyl)butane, formulated into (c) a topically applicable, cosmetically acceptable vehicle, diluent or carrier therefor.

25 Claims, No Drawings

DIBENZOYLMETHANE SUNSCREEN COMPOSITIONS CONTAINING PHOTOSTABILIZING AMOUNTS OF TRI-SUBSTITUTED BUTANE COMPOUNDS

CROSS-REFERENCE TO PRIORITY APPLICATION

This application claims priority under 35 U.S.C. §119 of FR-01/11139, filed Aug. 27, 2001, assigned to the assignee hereof and hereby expressly incorporated by reference.

BACKGROUND OF THE INVENTION

1. Technical Field of the Invention

This present invention relates to cosmetic or dermatological compositions suited for topical application, in particular for UV-photoprotecting human skin and hair, comprising, formulated into a cosmetically acceptable support (vehicle, diluent or carrier), (a) at least one UV screening agent of the dibenzoylmethane derivative type, and (b) a photostabilizing amount therefor of 1,1,1-tris(2-methyl-4-hydroxy-5-tert-butylphenyl)butane.

This invention also relates to a process for improving the stability of at least one dibenzoylmethane compound with respect to UV radiation, which entails combining said dibenzoylmethane compound with an effective amount of 1,1,1-tris(2-methyl-4-hydroxy-5-tert-butylphenyl)butane.

2. Description of the Prior Art

It is known to this art that light radiation having wavelengths of from 280 nm to 400 nm permits tanning of the human epidermis and that light rays having wavelengths more particularly from 280 to 320 nm, known as UV-B radiation, cause skin burns and erythema which can harm the development of a natural tan. For these reasons, as well as for aesthetic reasons, there is a constant demand for means of controlling this natural tanning in order, thus, to control the color of the skin; this UV-B radiation should thus be screened from the skin.

It is also known that UV-A radiation, having wavelengths from 320 to 400 nm, which causes tanning of the skin, is apt to induce adverse changes therein, in particular in the case of sensitive skin or skin which is continually exposed to solar radiation. UV-A rays cause, in particular, a loss of elasticity of the skin and the appearance of wrinkles promoting premature aging of the skin. They promote triggering of the erythemal reaction or amplify this reaction in certain individuals and may even be the cause of phototoxic or photoallergic reactions. Thus, for aesthetic and cosmetic reasons such as the conservation of the skin's natural elasticity, for example, an increasingly large number of individuals wish to control the effect of UV-A radiation on their skin. It is thus desirable to also screen out UV-A radiation.

Thus, with the goal of ensuring the most complete and most effective protection possible for the skin and the hair against the entire UV radiation spectrum, combinations of screening agents which are active in the UVA range and of screening agents which are active in the UVB range are generally formulated into sunscreen/antisun compositions.

In this respect, one particularly advantageous family of UV-A screening agents currently in favor includes dibenzoylmethane derivatives, and in particular 4-tert-butyl-4'-methoxydibenzoylmethane, which have high intrinsic absorbing power. These dibenzoylmethane derivatives, which are compounds which are now well known per se as screening agents that are active in the UV-A range, are described, in particular, in FR-A-2,326,405 and FR-A-2,440,933, as well as in EP-A-0,114,607; 4-(tert-butyl)-4'-methoxydibenzoyl-methane is moreover currently marketed under the trademark "Parsol 1789" by Hoffmann la Roche.

Unfortunately, it has been determined that dibenzoylmethane derivatives are compounds that are relatively sensitive to ultraviolet radiation (especially UV-A), i.e., more specifically, they have an annoying tendency to be degraded more or less quickly under the influence of this UV. Thus, this substantial lack of photochemical stability of dibenzoylmethane derivatives towards ultraviolet radiation, to which they are by nature intended to be subjected, does not make it possible to ensure constant protection during prolonged exposure to the sun, and so the user must make repeated applications at regular and close time intervals in order to obtain effective protection of the skin against UV rays.

1,3,5-Triazine derivatives are particularly desired in sunscreen/antisun cosmetics due to the fact that they are highly active in the UV-B range, and even in the UV-A range for certain of these compounds depending on the nature of the substituents involved. They are especially described in U.S. Pat. No. 4,367,390, EP-863,145, EP-517,104, EP-570,838, EP-507,691, EP-796,851, EP-775,698, EP-878,469 and EP-933,376, and the following are recognized, in particular:

2,4,6-tris[p-(2'-ethylhexyl-1'-oxycarbonyl)anilino]-1,3,5-triazine or "Ethylhexyl Triazone" (INCI name), marketed under the trademark "Uvinul T 150" by the company BASF, and 2-[(p-(tert-butylamido)anilino]-4,6-bis[(p-(2'ethylhexyl-1'-oxycarbonyl)anilino]-1,3,5-triazine or "Diethylhexyl Butamido Triazone" (INCI name), marketed under the trademark "Uvasorb HEB" by Sigma 3V.

However, it has been determined that when these 1,3,5-triazine derivatives are in the presence of dibenzoylmethane derivatives, in particular 4-tert-butyl-4'-methoxydibenzoylmethane, and under UV radiation, they present the drawback of undergoing substantial chemical degradation. Under these conditions, the combination of the two screening agents no longer provides a prolonged broad sunscreen/antisun protection to the skin and the hair.

SUMMARY OF THE INVENTION

It has now surprisingly and unexpectedly been determined that by combining with the dibenzoylmethane compounds indicated above an effective amount of 1,1,1-tris(2-methyl-4-hydroxy-5-tert-butylphenyl)butane, a substantial and noteworthy improvement in the photochemical stability (or photostability) of these same dibenzoylmethane derivatives is attained.

Furthermore, it too has been determined that incorporation of 1,1,1-tris(2-methyl-4-hydroxy-5-tert-butylphenyl) butane into a composition containing a combination of a dibenzoylmethane derivative with at least one 1,3,5-triazine derivative markedly enhances the photostability of this 1,3,5-triazine derivative in such compositions, and thus the overall efficacy thereof.

Accordingly, a major object of the present invention is the provision of cosmetic or dermatological compositions for topical application, comprising, formulated into a cosmetically acceptable support:

(a) at least one UV screening agent of the dibenzoylmethane derivative type, and (b) an effective photostabilizing amount of 1,1,1-tris(2-methyl-4-hydroxy-5-tert-butylphenyl)butane.

The present invention also features a process for improving the stability of at least one dibenzoylmethane compound in respect of UV radiation, which comprises combining said dibenzoylmethane derivative with an effective photostabilizing amount of 1,1,1-tris(2-methyl-4-hydroxy-5-tert-butylphenyl)butane.

The present invention thus features cosmetic or dermatological compositions for topical application, comprising, formulated into a cosmetically acceptable support:
(a) at least one UV screening agent of the dibenzoylmethane derivative type,
(b) at least one UV screening agent of the 1,3,5-triazine derivative type, and
(c) an effective amount of 1,1,1-tris(2-methyl4-hydroxy-5-tert-butylphenyl)butane.

Too, this invention features a process for improving the stability of at least one 1,3,5-triazine derivative in the presence of at least one dibenzoylmethane derivative vis-à-vis UV radiation, by adding thereto an effective amount of 1,1,1-tris(2-methyl-4-hydroxy-5-tert-butylphenyl)butane.

Thus, the present invention features including 1,1,1-tris(2-methyl-4-hydroxy-5-tert-butylphenyl)butane in cosmetic and dermatological compositions comprising at least one dibenzoylmethane derivative, for purpose of improving the stability of said dibenzoylmethane derivative versus UV irradiation.

Lastly, the present invention features incorporating 1,1,1-tris(2-methyl-4-hydroxy-5-tert-butylphenyl)butane into cosmetic or dermatological compositions comprising at least one dibenzoylmethane derivative and at least one 1,3,5-triazine derivative, for improving the stability of said 1,3,5-triazine derivative contained therein versus UV irradiation.

DETAILED DESCRIPTION OF BEST MODE AND SPECIFIC/PREFERRED EMBODIMENTS OF THE INVENTION

More particularly according to the present invention, by the expression "effective amount of 1,1,1-tris(2-methyl-4-hydroxy-5-tert-butylphenyl)butane in accordance with the invention" is intended an amount that is sufficient to provide an appreciable and significant improvement in the photostability of the dibenzoylmethane derivative(s) (or of the 1,3,5-triazine derivative(s)) of the photoprotective cosmetic composition. This minimum amount of photostabilizer to be formulated, which may vary depending on the nature of the cosmetically acceptable support selected for the composition, may be determined without any difficulty by means of a standard test of photostability measurement.

The 1,1,1-tris(2-methyl-4-hydroxy-5-tert-butylphenyl)butane compound corresponds to the following formula:

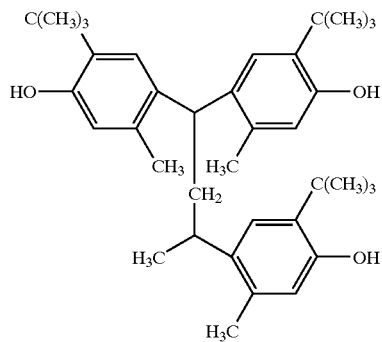

The 1,1,1-tris(2-methyl-4-hydroxy-5-tert-butylphenyl)butane compound is preferably present in the compositions of the invention in proportions ranging from 0.1% to 15% by weight and more preferably from 0.2% to 10% by weight relative to the total weight of the composition.

As indicated above, the dibenzoylmethane derivatives to be photostabilized in the context of the present invention are compounds that are already well known per se and described, especially, in FR-2,326,405, FR-2,440,933 and EP-0,114,607, hereby expressly incorporated by reference.

According to the present invention, one or more dibenzoylmethane derivatives may be employed.

Among the dibenzoylmethane derivatives according to the present invention, especially representative are:

2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane,
4,4'-diisopropyldibenzoylmethane,
4,4'-dimethoxydibenzoylmethane,
4-tert-butyl-4'-methoxydibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane, and
2,6-dimethyl-4-tert-butyl-4'-methoxydibenzoyl-methane.

Among the dibenzoylmethane compounds indicated above, most particularly preferred according to the present invention is 4-(tert-butyl)-4'-methoxydibenzoylmethane, especially the product marketed under the trademark "Parsol 1789" by Hoffmann la Roche, this screening agent thus corresponding to the following structural formula:

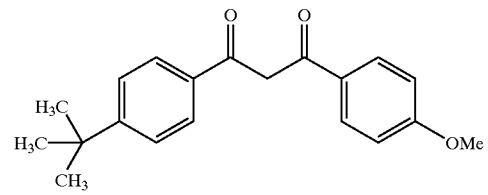

Another dibenzoylmethane derivative that is preferred according to the present invention is 4-isopropyldibenzoylmethane, a screening agent marketed under the trademark "Eusolex 8020" by Merck, and corresponding to the following structural formula:

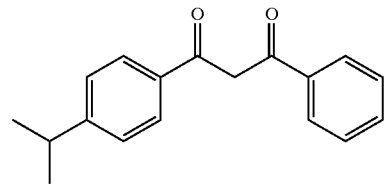

The dibenzoylmethane derivative(s) may be present in the compositions in accordance with the invention in contents preferably ranging from 0.1% to 15% by weight and more preferably from 0.5% to 10% by weight relative to the total weight of the composition.

Among the 1,3,5-triazine derivatives that are useful according to the present invention, preferred are those corresponding to formula (I) below:

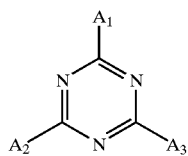

(I)

in which the radicals $A_1$, $A_2$ and $A_3$, which may be identical or different, are each selected from the groups of formula (II):

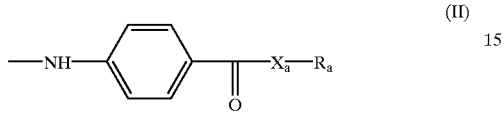

(II)

wherein the radicals $X_a$, which may be identical or different, are each oxygen or an —NH-group; the radicals $R_a$, which may be identical or different, are each hydrogen, an alkali metal, an ammonium radical optionally substituted with one or more alkyl or hydroxyalkyl radicals, a linear or branched $C_1$–$C_{18}$ alkyl radical, a $C_5$–$C_{12}$ cycloalkyl radical optionally substituted with one or more $C_1$–$C_4$ alkyl radicals, a polyoxyethylenated radical comprising from 1 to 6 ethylene oxide units, the terminal OH group of which is methylated, a radical of formula (III), (IV) or (V) below:

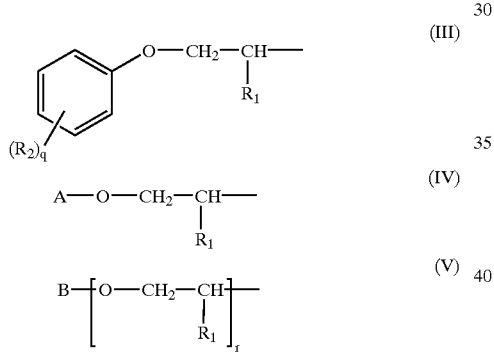

in which $R_1$ is hydrogen or a methyl radical; $R_2$ is a $C_1$–$C_9$ alkyl radical; q is an integer ranging from 0 to 3; r is an integer ranging from 1 to 10; A is a $C_4$–$C_8$ alkyl radical, or a $C_5$–$C_8$ cycloalkyl radical; and B is a linear or branched $C_1$–$C_8$ alkyl radical, a $C_5$–$C_8$ cycloalkyl radical, or an aryl radical optionally substituted with one or more $C_1$–$C_4$ alkyl radicals.

A first family of 1,3,5-triazine derivatives that is more particularly preferred is described especially in EP-A-0,517, 104, and is that of the 1,3,5-triazines corresponding to formula (I) in which $A_1$, $A_2$ and $A_3$ are of formula (II) and have the following characteristics:

one of the groups $X_a$—$R_a$ is a radical —NH—$R_a$ wherein $R_a$ is a $C_5$–$C_{12}$ cycloalkyl radical optionally substituted with one or more $C_1$–$C_4$ alkyl radicals, or a radical of formula (III), (IV) or (V) above in which B is a $C_1$–$C_4$ alkyl radical; $R_2$ is a methyl radical; the other 2 groups $X_a$—$R_a$ are each a radical —O—$R_a$ wherein $R_a$, which may be identical or different, are each hydrogen, an alkali metal, an ammonium radical optionally substituted with one or more alkyl or hydroxyalkyl radicals, a linear or branched $C_1$–$C_{18}$ alkyl radical, a $C_5$–$C_{12}$ cycloalkyl radical optionally substituted with one or more $C_1$–$C_4$ alkyl radicals, or a radical of formula (III), (IV) or (V) above in which B is a $C_1$–$C_4$ alkyl radical, and $R_2$ is a methyl radical.

A second family of 1,3,5-triazine derivatives that is more particularly preferred is described especially in EP-A-0,570, 838, i.e., 1,3,5-triazines corresponding to formula (I) in which $A_1$, $A_2$ and $A_3$ are of formula (II) and have all of the following characteristics:

one or two groups $X_a$—$R_a$ is a radical —NH—$R_a$, wherein $R_a$ is a linear or branched $C_1$–$C_{18}$ alkyl radical; a $C_5$–$C_{12}$ cycloalkyl radical optionally substituted with one or more $C_1$–$C_4$ alkyl radicals; or a radical of formula (III), (IV) or (V) above in which B is a $C_1$–$C_4$ alkyl radical; $R_2$ is a methyl radical; and the other or the other two group(s) $X_a$—$R_a$ being a radical —O—$R_a$ wherein the groups $R_a$, which may be identical or different, are each hydrogen, an alkali metal, an ammonium radical optionally substituted with one or more alkyl or hydroxyalkyl radicals, a linear or branched $C_1$–$C_{18}$ alkyl radical, a $C_5$–$C_{12}$ cycloalkyl radical optionally substituted with one or more $C_1$–$C_4$ alkyl radicals, a radical of formula (III), (IV) or (V) above in which B is a $C_1$–$C_4$ alkyl radical, and $R_2$ is a methyl radical.

A 1,3,5-triazine of this second family that is particularly preferred is 2-[(p-(tert-butylamido)-anilino]-4,6-bis [(p-(2'-ethylhexyl-1'-oxycarbonyl)-anilino]-, 3,5-triazine or "Diethylhexyl Butamido Triazone" marketed under the trademark "Uvasorb HEB" by Sigma 3V and corresponding to the following formula:

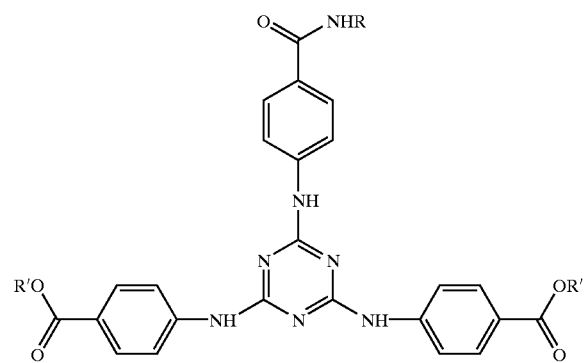

in which R' denotes a 2-ethylhexyl radical and R denotes a tert-butyl radical.

A third preferred family of compounds that is suited for formulation into the compositions of the present invention is particularly described in U.S. Pat. No. 4,724,137, i.e., the 1,3,5-triazines corresponding to formula (I) in which $A_1$, $A_2$ and $A_3$ are of formula (II) and have the following characteristics:

$X_a$ are identical and represent oxygen;

the groups $R_a$, which may be identical or different, are each a $C_6$–$C_{12}$ alkyl radical or a polyoxyethylenated radical comprising from 1 to 6 ethylene oxide units and in which the terminal OH group is methylated.

A 1,3,5-triazine of this third family that is particularly preferred is 2,4,6-tris[p-(2'-ethylhexyl-1'-oxycarbonyl) anilino]-1,3,5-triazine or "Ethylhexyl Triazone" marketed, especially, under the trademark "Uvinul T 150" by BASF and corresponds to the following formula:

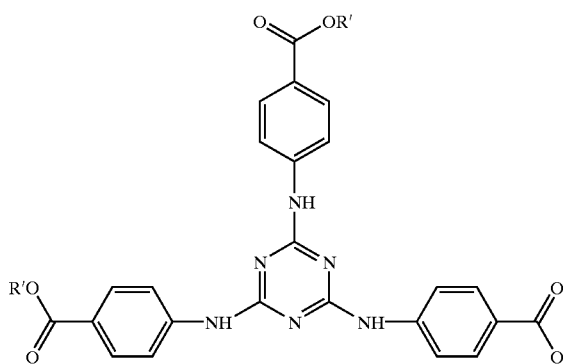

in which R' is a 2-ethylhexyl radical.

The 1,3,5-triazine derivative(s) is (are) generally present in the compositions of the invention in a content that can range from 0.1% to 15% and preferably from 0.5% to 10% by weight relative to the total weight of the composition.

The compositions in accordance with the invention may also comprise other additional organic UV screening agents that are active in the UVA and/or UVB range (absorbers), which are water-soluble or liposoluble or even insoluble in the cosmetic solvents commonly used.

The additional organic UV screening agents are especially selected from among anthranilates; salicylic derivatives; camphor derivatives; benzophenone derivatives; β,β-diphenylacrylate derivatives; benzotriazole derivatives; benzalmalonate derivatives; benzimidazole derivatives; triazine derivatives other than those of formula (I) indicated above; imidazolines; bis-benzazolyl derivatives as described in EP-669,323 and U.S. Pat. No. 2,463,264; p-aminobenzoic acid (PABA) derivatives; methylenebis(hydroxyphenyl)benzotriazole derivatives as described in U.S. Pat. Nos. 5,237,071, 5,166,355, GB-2,303,549, DE-197,26,184 and EP-893,119; screening polymers and screening silicones such as those particularly described in WO-93/04665; dimers derived from α-alkylstyrene, such as those described in DE-198,55,649, 4,4-diarylbutadienes such as those described in EP-0,967,200 and DE-197,55,649 (each hereby expressly incorporated by reference).

Exemplary UV-A-active and/or UV-B-active additional organic screening agents include the following, denoted hereinbelow under their INCI name:

Para-Aminobenzoic Acid Derivatives
PABA,
Ethyl PABA,
Ethyl dihydroxypropyl PABA,
Ethylhexyl dimethyl PABA marketed, in particular, under the trademark "Escalol 507" by ISP,
Glyceryl PABA,
PEG-25 PABA marketed under the trademark "Uvinul P25" by BASF.

Salicylic Derivatives
Homosalate marketed under the trademark "Eusolex HMS" by Rona/EM Industries,
Ethylhexyl salicylate marketed under the trademark "Neo Heliopan OS" marketed by Haarmann and Reimer,
Dipropylene glycol salicylate marketed under the trademark "Dipsal" by Scher,
TEA salicylate marketed under the trademark "Neo Heliopan TS" by Haarmann and Reimer.

β,β'-Diphenyl Acrylate Derivatives
Octocrylene marketed, in particular, under the trademark "Uvinul N539" by BASF,
Etocrylene marketed, in particular, under the trademark "Uvinul N35" by BASF.

Benzophenone Derivatives
Benzophenone-1 marketed under the trademark "Uvinul 400" by BASF,
Benzophenone-2 marketed under the trademark "Uvinul D50" by BASF,
Benzophenone-3 or Oxybenzone marketed under the trademark "Uvinul M40" by BASF,
Benzophenone-4 marketed under the trademark "Uvinul MS40" by BASF,
Benzophenone-5,
Benzophenone-6 marketed under the trademark "Helisorb 11" by Norquay,
Benzophenone-8 marketed under the trademark "Spectra-Sorb UV-24" by American Cyanamid,
Benzophenone-9 marketed under the trademark "Uvinul DS-49" by BASF,
Benzophenone-12.

Benzylidenecamphor Derivatives
4-Methylbenzylidenecamphor marketed under the trademark "Eusolex 6300" by Merck,
3-Benzylidenecamphor marketed under the trademark "Mexoryl SD" by Chimex,
Benzylidenecamphorsulfonic acid marketed under the trademark "Mexoryl SL" by Chimex,
Camphor benzalkonium methosulfate marketed under the trademark "Mexoryl SO" by Chimex,
Terephthalylidenedicamphorsulfonic acid marketed under the trademark "Mexoryl SX" by Chimex,
Polyacrylamidomethylbenzylidenecamphor marketed under the trademark "Mexoryl SW" by Chimex.

Benzimidazole Derivatives
Phenylbenzimidazolesulfonic acid marketed, in particular, under the trademark "Eusolex 232" by Merck,
Disodium phenyldibenzimidazole tetrasulfonate marketed under the trademark "Neo Heliopan AP" by Haarmann and Reimer.

Triazine Derivatives
Anisotriazine marketed under the trademark "Tinosorb S" by Ciba Geigy, 2,4,6-tris-(diisobutyl 4'-amino-benzalmalonate)-s triazine.

Benzotriazole Derivatives
Methylenebis(benzotriazolyl)tetramethylbutylphenol marketed in solid form under the trademark "Mixxim BB/100" by Fairmount Chemical, or in micronized form as an aqueous dispersion under the trademark "Tinosorb M" by Ciba Specialty Chemicals,
Drometrizole trisiloxane marketed under the trademark "Silatrizole" by Rhodia Chimie.

Anthranilic Derivatives
Menthyl anthranilate marketed under the trademark "Neo Heliopan MA" by Haarmann and Reimer.

Imidazoline Derivatives
Ethylhexyldimethoxybenzylidenedioxoimidazoline propionate.

Benzalmalonate Derivatives
Polyorganosiloxane containing benzalmalonate functional groups marketed under the trademark "Parsol SLX" by Hoffmann La Roche and mixtures thereof.

The additional organic UV screening agents that are more particularly preferred are selected from among the following compounds:

Ethylhexyl salicylate,
Octocrylene,
Phenylbenzimidazolesulfonic acid,
4-Methylbenzylidenecamphor,
Disodium phenyldibenzimidazole tetrasulfonate, Terephthalylidenedicamphorsulfonic acid,
Anisotriazine,
2,4,6-Tris-(4'-Amino-benzalmalonatediisobutyl)-s-triazine,
Benzophenone-3,
Benzophenone-4,
Benzophenone-5,
Methylenebis(benzotriazolyl)tetramethylbutylphenol,
n-Hexyl 2-(4-diethylamino-2-hydroxybenzoyl)-benzoate
Drometrizole trisiloxane, and mixtures thereof.

The cosmetic compositions according to the invention may also comprise pigments or nanopigments (average size of the primary particles: generally ranging from 5 nm to 100 nm and preferably from 10 nm to 50 nm) of coated or uncoated metal oxides, such as, for example, nanopigments of titanium dioxide (amorphous or crystallized in rutile and/or anatase form), of iron oxide, of zinc oxide, of zirconium oxide or of cerium oxide, which are all UV photoprotective agents that are well known per se. Standard coating agents are, moreover, alumina and/or aluminum stearate. Such coated or uncoated metal oxide nanopigments are described, in particular, in EP-A-0,518,772 and EP-A-0,518,773.

The compositions according to the invention may also contain agents for artificially tanning and/or browning the skin (self-tanning agents) such as, for example, dihydroxyacetone (DHA).

The compositions of the invention may also comprise standard cosmetic additives and adjuvants selected especially from among fatty substances, organic solvents, ionic or nonionic thickeners, softeners, antioxidants, free-radical scavengers, opacifiers, stabilizers, emollients, silicones, α-hydroxy acids, antifoams, moisturizers, vitamins, insect repellants, fragrances, preservatives, surfactants, anti-inflammatories, substance P antagonists, fillers, polymers, propellants, acidifying or basifying agents, colorants or any other ingredient usually formulated into cosmetics, in particular for the production of sunscreen compositions in the form of emulsions.

The fatty substances may be an oil or a wax or mixtures thereof, and they also comprise linear or cyclic fatty acids, fatty alcohols and fatty acid esters such as benzoic, trimellitic and hydroxybenzoic acid derivatives. The oils may be selected from among animal, plant, mineral and synthetic oils and especially from liquid petroleum jelly, liquid paraffin, volatile or non-volatile silicone oils, isoparaffins, polyolefins, fluoro oils and perfluoro oils. Similarly, the waxes may be animal, fossil, plant, mineral and synthetic waxes that are known per se.

Among the organic solvents, exemplary are the lower alcohols and polyols.

Of course, one skilled in this art will take care to select this or these optional additional compound(s) and/or the amounts thereof such that the advantageous properties, in particular the photostability, intrinsically associated with the compositions in accordance with the invention are not, or are not substantially, adversely affected by the envisaged addition(s).

The compositions of the invention may be formulated according to techniques that are well known to this art, in particular those intended for preparing emulsions of oil-in-water or water-in-oil type.

These compositions may be, in particular, in the form of a simple emulsion or a complex emulsion (O/W, W/O, O/W/O or W/O/W), such as a cream, a milk, a lotion, a gel or a cream-gel, a powder or a solid tube, and may optionally be packaged as an aerosol and may be in the form of a mousse or spray.

When it is an emulsion, the aqueous phase of this emulsion may comprise a nonionic vesicular dispersion prepared according to known processes (Bangham, Standish and Watkins, *J. Mol. Biol.* 13, 238 (1965), FR-2,315,991 and FR-2,416,008).

The cosmetic compositions of the invention are useful for protecting the human epidermis or the hair against the damaging effects of ultraviolet rays, as sunscreen/antisun compositions or as makeup products.

When the cosmetic composition according to the invention is used for protecting the human epidermis against UV radiation, or as an antisun/sunscreen composition, it may be in the form of a suspension or a dispersion in solvents or fatty substances, in the form of a nonionic vesicular dispersion, or in the form of an emulsion, preferably of oil-in-water type, such as a milk, lotion or a cream, or in the form of an ointment, a gel, a cream-gel, a solid tube, a powder, a stick, an aerosol mousse or a spray.

When the cosmetic composition according to the invention is used for protecting the hair against UV rays, it may be formulated as a shampoo, a lotion, a gel, an emulsion or a nonionic vesicular dispersion and may constitute, for example, a rinse-out composition, to be applied before or after shampooing, before or after dyeing or bleaching, or before, during or after permanent-waving or straightening the hair, a styling or treating lotion or gel, a blow-drying or hairsetting lotion or gel, or a permanent-waving, straightening, dyeing or bleaching composition for the hair.

When the composition is suited as a makeup product for the eyelashes, the eyebrows or the skin, such as an epidermal treatment cream, a foundation, a tube of lipstick, an eyeshadow, a face powder, mascara or an eyeliner, it may be in solid or pasty, anhydrous or aqueous form, for example oil-in-water or water-in-oil emulsions, nonionic vesicular dispersions or suspensions.

For example, for the sunscreen/antisun formulations in accordance with the invention that contain a support of oil-in-water emulsion type, the aqueous phase (especially comprising the hydrophilic screening agents) generally constitutes from 50% to 95% by weight and preferably from 70% to 90% by weight, relative to the total weight of the formulation, the oily phase (especially comprising the lipophilic screening agents) from 5% to 50% by weight and preferably from 10% to 30% by weight, relative to the total weight of the formulation, and the (co)emulsifier(s) from 0.5% to 20% by weight and preferably from 2% to 10% by weight, relative to the total weight of the formulation.

As indicated above, the present invention features compositions cosmetic or dermatological applications for protecting the skin and/or the hair against ultraviolet radiation, in particular solar radiation.

This invention also features improving the stability of at least one dibenzoylmethane compound in respect as UV radiation protection, which entails combining such dibenzoylmethane compound with an effective amount of 1,1,1-tris(2-methyl-4-hydroxy-5-tert-butylphenyl)butane as defined above.

The present invention also features 1,1,1-tris(2-methyl-4-hydroxy-5-tert-butylphenyl)butane into cosmetic or dermatological compositions comprising at least one UV screening agent of the dibenzoylmethane derivative type, for the purpose of improving the stability of said dibenzoylmethane compound in respect of UV radiation.

Too, this invention, thus, also features a regime or regimen for UV-photoprotecting human skin and/or hair against the damaging effects of UV-radiation, by topically applying thereon, for such period of time as required to provide the desired UV-photoprotective effect, any of the subject UV-photoprotecting cosmetic/dermatological compositions.

In order to further illustrate the present invention and the advantages thereof, the following specific examples are given, it being understood that same are intended only as illustrative and in nowise limitative.

EXAMPLE 1

The photostability of the dibenzoylmethane compound was evaluated on several formulations in which the amount of 1,1,1-tris(2-methyl-4-hydroxy-5-tert-butylphenyl)butane (X) was varied. The support common to these formulations was as follows:

TABLE I

| Support 1 | % by weight |
| --- | --- |
| C12/C15 Alkyl benzoate (Witconol TN - Witco) | 15.00 |
| Butylmethoxydibenzoylmethane (Parsol 1789 - Hoffmann la Roche) | 2 |
| 1,1,1-Tris(2-methyl-4-hydroxy-5-tert-butylphenyl)butane (Mixxim AO-30 - Fairmount Chemical) | x |
| Oxyethylenated (200 EO) acrylic acid/monostearyl itaconate copolymer (Structure 2001 - National Starch) | 3.33 |
| Triethanolamine | 0.45 |
| Preservatives | 1.20 |
| Demineralized water qs | 100 |

Measurement Techniques

For each formula, 3 test samples and 3 control samples were prepared. 2 mg/cm$^2$ of formula were deposited by spatula onto polymethyl methacrylate plates. The test plates were exposed for 1 hour, 39 minutes, to a Sun Test Heraus machine equipped with a xenon lamp and having as UV-A illumination: $3.02 \times 10^{-3}$ W/cm$^2$, and as UV-B illumination: $2.1 \times 10^{-4}$ W/cm$^2$, and the control plates were maintained for the same time and at the same temperature (38–40° C.) in darkness. After this time, the screening agents were extracted by immersing each plate in 50 g of ethanol and subjecting them to ultrasound for 15 minutes to ensure good extraction.

The solutions obtained were analyzed by UV spectrometry. For each test formula, the amount of residual butylmethoxydibenzoylmethane after exposure is given as the ratio of its optical density (OD) in the exposed sample to its unexposed optical density (OD). The machine was set at the maximum absorption corresponding to the butylmethoxydibenzoylmethane:

$\lambda_{max}$=355 nm.

The results obtained reported collated in Table II below:

TABLE II

| X (% by weight) | Residual OD at 358 nm after 1 hour of UVA irradiation |
| --- | --- |
| 0 | 11 ± 1% |
| 0.5 | 21 ± 1% |
| 1 | 37 ± 1% |
| 2 | 60 ± 2% |

EXAMPLE 2

The photostability of octyltriazone in the presence of butylmethoxydibenzoylmethane was examined on several formulations in which the amount of 1,1,1-tris(2-methyl-4-hydroxy-5-tert-butylphenyl)butane (X) was varied. The support common to these formulations was as follows:

TABLE III

| Support 2 | % by weight |
| --- | --- |
| C12/C15 Alkyl benzoate (Witconol TN - Witco) | 15.00 |
| Butylmethoxydibenzoylmethane (Parsol 1789 - Hoffmann la Roche) | 0.5 |
| 1,1,1-Tris(2-methyl-4-hydroxy-5-tert-butylphenyl)butane (Mixxim AO-30 - Fairmount Chemical | x |
| Oxyethylenated (Uvinul T150 - BASF) | 1.5 |
| Oxyethylenated (200 EO) acrylic acid/monostearyl itaconate copolymer (Structure 2001 - National Starch) | 3.33 |
| Triethanolamine | 0.45 |
| Preservatives | 1.20 |
| Demineralized water qs | 100 |

Measurement Technique

For each formula, 3 test samples and 3 control samples were prepared. 2 mg/cm$^2$ of formula were deposited by spatula onto polymethyl methacrylate plates. The test plates were exposed for 1 hour, 39 minutes, to a Sun Test Heraus machine equipped with a xenon lamp and having as UV-A illumination: $3.02 \times 10^{-3}$ W/cm$^2$, and as UV-B illumination: $2.1 \times 10^{-4}$ W/cm$^2$, and the control plates were maintained for the same time and at the same temperature (38–40° C.) in darkness. After this time, the screening agents were extracted by immersing each plate in 50 g of ethanol and subjecting them to ultrasound for 15 minutes to ensure good extraction.

The solutions obtained were analyzed by UV spectrometry. For each test formula, the amount of residual butylmethoxydibenzoylmethane and the residual amount of octyltriazone after exposure is given as the ratio of each respective optical density (OD) in the exposed sample to the unexposed optical density (OD) corresponding to each filter. The machine was set at the maximum absorption corresponding to each filter:

Butylmethoxydibenzoylmethane: $\lambda_{max}$=358 nm

Octyltriazone: $\lambda_{max}$=312 nm

The results obtained are reported in Table IV below:

TABLE IV

| X (% by weight) | Residual OD of the dibenzoylmethane at 358 nm after 1 hour of UVA irradiation | Residual OD of the triazine at 312 nm after 1 hour of UVA irradiation |
| --- | --- | --- |
| 0 | 32 ± 4% | 87 ± 13% |
| 3 | 84 ± 9% | 98 ± 12% |

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable UV-photoprotecting cosmetic/dermatological composition, comprising (a) a UV-photoprotective amount of at least one dibenzoylmethane sunscreen, and (b) an effective sunscreen photostabilizing amount of 1,1,1-tris(2-methyl-4-hydroxy-5-tertbutylphenyl)butane, formulated into (c) a topically applicable, cosmetically acceptable vehicle, diluent or carrier therefor.

2. A topically applicable UV-photoprotecting cosmetic/dermatological composition, comprising (a) a UV-photoprotective amount of at least one dibenzoylmethane sunscreen, (a') a UV-photoprotective amount of at least one 1,3,5-triazine sunscreen, and (b) an effective photostabilizing amount of 1,1,1-tris(2-methyl-4-hydroxy-5-tert-butylphenyl)butane, formulated into (c) a topically applicable, cosmetically acceptable vehicle, diluent or carrier therefor.

3. A UV-photoprotecting cosmetic/dermatological composition as defined by claims 1 or 2, said at least one dibenzoylmethane sunscreen being selected from the group consisting of 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxydibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, and 2,6-dimethyl-4-tert-butyl-4'-methoxydibenzoylmethane.

4. The UV-photoprotecting cosmetic/dermatological composition as defined by claim 3, said at least one dibenzoylmethane sunscreen comprising 4-(tert-butyl)-4'-methoxydibenzoylmethane.

5. The UV-photoprotecting cosmetic/dermatological composition as defined by claim 3, said at least one dibenzoylmethane sunscreen comprising 4-isopropyldibenzoylmethane.

6. The UV-photoprotecting cosmetic/dermatological composition as defined by claims 1 or 2, said 1,1,1-tris(2-methyl-4-hydroxy-5-tert-butylphenyl)butane comprising from 0.1% to 15% by weight thereof.

7. The UV-photoprotecting cosmetic/dermatological composition as defined by claims 1 or 2, said at least one dibenzoylmethane sunscreen comprising from 0.1% to 15% by weight thereof.

8. The UV-photoprotecting cosmetic/dermatological composition as defined by claim 2, said at least one 1,3,5-triazine sunscreen having the formula (I) below:

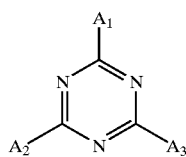

in which the radicals $A_1$, $A_2$ and $A_3$, which may be identical or different, are each a radical of formula (II) below:

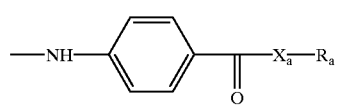

wherein the radicals $X_a$, which may be identical or different, are each oxygen or an —NH— radical; and the radicals $R_a$, which may be identical or different, are each hydrogen, an alkali metal, an ammonium radical optionally substituted with one or more alkyl or hydroxyalkyl radicals, a linear or branched $C_1$–$C_{18}$ alkyl radical, a $C_5$–$C_{12}$ cycloalkyl radical optionally substituted with one or more $C_1$–$C_4$ alkyl radicals, a polyoxyethylenated radical comprising from 1 to 6 ethylene oxide units, the terminal OH group of which is methylated, or a radical of formula (III), (IV) or (V) below:

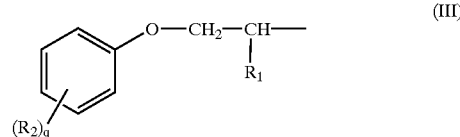

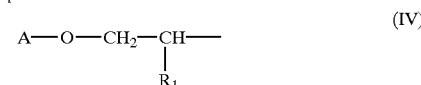

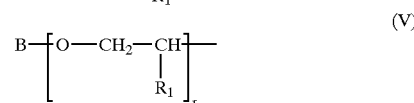

wherein $R_1$ is hydrogen or a methyl radical; $R_2$ is a $C_1$–$C_9$ alkyl radical; q is an integer ranging from 0 to 3; r is an integer ranging from 1 to 10; A is a $C_4$–$C_8$ alkyl radical, or a $C_5$–$C_8$ cycloalkyl radical; and B is a linear or branched $C_4$–$C_8$ alkyl radical, a $C_5$–$C_8$ cycloalkyl radical, or an aryl radical optionally substituted with one or more $C_1$–$C_4$ alkyl radicals.

9. The UV-photoprotecting cosmetic/dermatological composition as defined by claim 8, wherein the compound of formula (I), each of $A_1$, $A_2$ and $A_3$ is of formula (II) and has all of the following characteristics:
  one of the groups $X_a$—$R_a$ is a radical —NH—$R_a$ wherein $R_a$ is a $C_5$–$C_{12}$ cycloalkyl radical optionally substituted with one or more $C_1$–$C_4$ alkyl radicals, or a radical of formula (III), (IV) or (V) in which:
  B is a $C_1$–$C_4$ alkyl radical;
  $R_2$ is a methyl radical;
  the other 2 groups $X_a$—$R_a$ are each a radical —O—$R_a$ wherein the radicals $R_a$, which may be identical or different, are each hydrogen, an alkali metal, an ammonium radical optionally substituted with one or more alkyl or hydroxyalkyl radicals, a linear or branched $C_1$–$C_{18}$ alkyl radical, a $C_5$–$C_{12}$ cycloalkyl radical optionally substituted with one or more $C_1$–$C_4$ alkyl radicals, or a radical of formula (III), (IV) or (V) above in which:
  B is a $C_1$–$C_4$ alkyl radical;
  $R_2$ is a methyl radical.

10. The UV-photoprotecting cosmetic/dermatological composition as defined by claim 8, wherein the compound of formula (I), each of $A_1$, $A_2$ and $A_3$ is of formula (II) and has all of the following characteristics:
  one or two groups $X_a$—$R_a$ represent a radical —NH—$R_a$, wherein $R_a$ is a linear or branched $C_1$–$C_{18}$ alkyl radical, a $C_5$–$C_{12}$ cycloalkyl radical optionally substituted with one or more $C_1$–$C_4$ alkyl radicals, or a radical of formula (III), (IV) or (V) in which:
  B is a $C_1$–$C_4$ alkyl radical;
  $R_2$ is a methyl radical;
  the other or the other two group(s) $X_a$—$R_a$ being a radical —O—$R_a$ wherein the radicals $R_a$, which may be identical or different, are each hydrogen, an alkali metal, an ammonium radical optionally substituted with one or more alkyl or hydroxyalkyl radicals, a linear or branched $C_1$–$C_{18}$ alkyl radical, a $C_5$–$C_{12}$ cycloalkyl radical optionally substituted with one or more $C_1$–$C_4$ alkyl radicals, or a radical of formula (III), (IV) or (V) above in which:
B is a $C_1$–$C_4$ alkyl radical;
$R_2$ is a methyl radical.

11. The UV-photoprotecting cosmetic/dermatological composition as defined by claim 8, said compound of formula (I) being 2-[(p-(tert-butylamido)anilino]-4,6-bis[(p-(2'-ethylhexyl-1'-oxycarbonyl)anilino]-1,3,5-triazine, having the following structural formula:

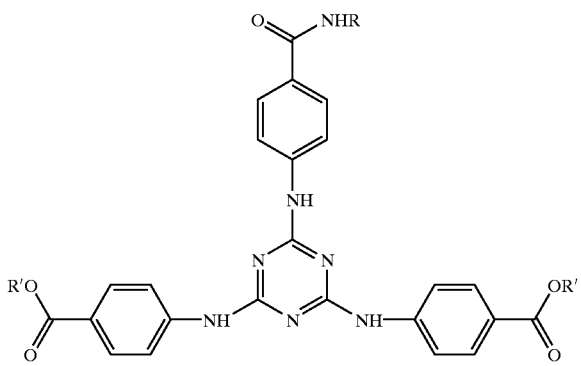

in which R' is a 2-ethylhexyl radical and R is a tert-butyl radical.

12. The UV-photoprotecting cosmetic/dermatological composition as defined by claim 8, wherein the compound of formula (I), each of $A_1$, $A_2$ and $A_3$ is of formula (II) and has all of the following characteristics:
the radicals $X_a$ are identical and each is oxygen; and
the radicals $R_a$, which may be identical or different, each are a $C_6$–$C_{12}$ alkyl radical or a polyoxyethylenated radical comprising from 1 to 6 ethylene oxide units and in which the terminal OH group is methylated.

13. The UV-photoprotecting cosmetic/dermatological composition as defined by claim 12, which the compound of formula (I) is 2,4,6-tris[p-(2'-ethylhexyl-1'-oxycarbonyl) anilino]-1,3,5-triazine and has following structural formula:

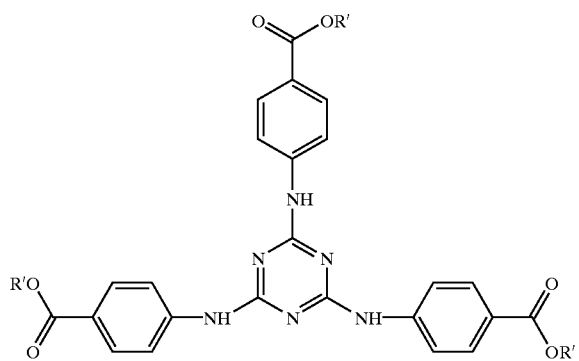

in which R' is a 2-ethylhexyl radical.

14. The UV-photoprotecting cosmetic/dermatological composition as defined by claim 2, said at least one 1,3,5-triazine sunscreen comprising from 0.1% to 15% by weight thereof.

15. The UV-photoprotecting cosmetic/dermatological composition as defined by claims 1 or 2, further comprising at least one other organic sunscreen that is active in the UV-A and/or UV-B range.

16. The UV-photoprotecting cosmetic/dermatological composition as defined by claim 15, said at least one other organic sunscreen being selected from the group consisting of anthranilates; salicylic derivatives; camphor derivatives; benzophenone derivatives; triazine derivatives other than those of formula (I); β,β-diphenylacrylate derivatives; benzotriazole derivatives; benzalmalonate derivatives; benzimidazole derivatives; imidazolines; bis-benzazolyl derivatives; p-aminobenzoic acid (PABA) derivatives; methylenebis (hydroxyphenyl)benzotriazole derivatives; screening polymers and screening silicones; dimers derived from α-alkylstyrene; 4,4-diarylbutadienes, and mixtures thereof.

17. The UV-photoprotecting cosmetic/dermatological composition as defined by claim 16, said at least one other organic sunscreen being selected from the group consisting of:

Ethylhexyl salicylate,
Octocrylene,
Phenylbenzimidazolesulfonic acid,
4-Methylbenzylidenecamphor,
Disodium phenyldibenzimidazole tetrasulfonate,
Terephthalylidenedicamphorsulfonic acid,
Anisotriazine,
2,4,6-Tris-(diisobutyl-4'-amino-benzalmalonate)-s-triazine,
Benzophenone-3,
Benzophenone-4,
Benzophenone-5,
n-Hexyl 2-(4-diethylamino-2-hydroxybenzoyl)-benzoate,
Methylenebis(benzotriazolyl)tetramethylbutylphenol,
Drometrizole trisiloxane and mixtures thereof.

18. The UV-photoprotecting cosmetic/dermatological composition as defined by claims 1 or 2, further comprising coated or uncoated metal oxide pigments or nanopigments.

19. The UV-photoprotecting cosmetic/dermatological composition as defined by claim 18, said pigments or nanopigments comprising titanium dioxide, zinc oxide, iron oxide, zirconium oxide or cerium oxide, and mixtures thereof, whether coated or uncoated.

20. The UV-photoprotecting cosmetic/dermatological composition as defined by claims 1 or 2, further comprising at least one agent for artificially tanning and/or browning the skin.

21. The UV-photoprotecting cosmetic/dermatological composition as defined by claims 1 or 2, further comprising at least one adjuvant or additive selected from the group consisting of fatty substances, organic solvents, ionic or nonionic thickeners, softeners, antioxidants, free-radical scavengers, opacifiers, stabilizers, emollients, silicones, α-hydroxy acids, antifoams, moisturizers, vitamins, insect repellents, fragrances, preservatives, surfactants, anti-inflammatories, substance P antagonists, fillers, polymers, propellants, basifying or acidifying agents, colorants and mixtures thereof.

22. The UV-photoprotecting cosmetic/dermatological composition as defined by claims 1 or 2, formulated as a nonionic vesicular dispersion, an emulsion, a cream, a milk, a lotion, a gel, a cream-gel, a suspension, a dispersion, a powder, a solid tube, a shampoo, a mousse or a spray.

23. The UV-photoprotecting cosmetic/dermatological composition as defined by claims 1 or 2, comprising a makeup for the eyelashes, the eyebrows or the skin and formulated in solid or pasty, anhydrous or aqueous form, or in the form of an emulsion, a suspension or a dispersion.

24. A process for improving the UV-photostability of at least one dibenzoylmethane sunscreen, or combination of at least one dibenzoylmethane sunscreen with at least one 1,3,5-triazine sunscreen, comprising formulating therewith an effective sunscreen photostabilizing amount of 1,1,1-tris (2-methyl-4-hydroxy-5-tert-butylphenyl)butane.

25. A regime or regimen for UV-photoprotecting human skin and/or hair against the damaging effects of UV-radiation, comprising topically applying thereon, for such period of time as required to provide the desired effect, an effective amount of the UV-photoprotecting cosmetic/dermatological composition as defined by claims 1 or 2.

* * * * *